United States Patent [19]

Marcilly et al.

[11] Patent Number: 5,456,822
[45] Date of Patent: Oct. 10, 1995

[54] CATALYST OF THE GALLOALUMINOSILICATE TYPE CONTAINING GALLIUM, A NOBEL METAL OF THE PLATINUM FAMILY AND AT LEAST ON ADDITIONAL METAL, AND ITS USE IN THE AROMATIZATION OF HYDROCARBONS

[75] Inventors: Christian Marcilly, Houilles; Fabio Alario, La Varenne; Jean-Francois Joly, Paris; Fabienne Le Peltier, Rueil Malmaison, all of France

[73] Assignee: Institut Francais du Petrole, Rueil Malmaison, France

[21] Appl. No.: 141,000

[22] Filed: Oct. 26, 1993

Related U.S. Application Data

[62] Division of Ser. No. 863,658, Apr. 6, 1992, Pat. No. 5,281,566.

[30] Foreign Application Priority Data

Apr. 4, 1991 [FR] France .................. 91 04.224

[51] Int. Cl.$^6$ .................. C10G 35/095; C10G 35/085
[52] U.S. Cl. .................. 208/136; 208/137; 208/138; 585/415
[58] Field of Search .................. 565/415; 208/136, 208/137, 138

[56] References Cited

U.S. PATENT DOCUMENTS

| | | | |
|---|---|---|---|
| 4,036,741 | 7/1977 | Pollitzer et al. | 208/139 |
| 4,072,731 | 2/1978 | Rausch | 208/139 |
| 4,214,980 | 7/1980 | Le Page et al. | 208/139 |
| 4,497,969 | 2/1985 | Ball et al. | 585/415 |
| 4,585,641 | 2/1986 | Barri et al. | 502/61 |
| 4,590,322 | 5/1986 | Chu | 585/415 |
| 4,652,688 | 3/1987 | Brophy et al. | 585/408 |
| 4,727,206 | 2/1988 | Clayson et al. | 585/415 |
| 4,761,511 | 8/1988 | Barlow | 585/415 |
| 4,766,265 | 8/1988 | Desmond et al. | 585/415 |
| 4,806,699 | 2/1989 | Smith et al. | 585/314 |
| 4,808,763 | 2/1989 | Shum | 585/415 |
| 4,839,320 | 6/1989 | Trowbridge et al. | 502/66 |
| 4,861,740 | 8/1989 | Sachtler et al. | 502/66 |
| 4,861,934 | 8/1989 | Suzuki et al. | 502/66 |
| 4,886,927 | 12/1989 | Sachtler et al. | 585/481 |
| 4,911,823 | 3/1990 | Chen et al. | 208/67 |
| 4,922,051 | 5/1990 | Nemet-Mavrodin et al. | 585/418 |
| 4,922,055 | 5/1990 | Chu | 585/470 |
| 4,923,835 | 5/1990 | Travers et al. | 502/66 |
| 4,950,028 | 8/1990 | Harrison | 303/115 |
| 5,010,048 | 4/1991 | Petit et al. | 502/61 |
| 5,026,921 | 6/1991 | Degnan, Jr. et al. | 585/415 |
| 5,043,306 | 8/1991 | Shum | 502/61 |
| 5,073,673 | 12/1991 | Hirabayashi et al. | 585/415 |
| 5,128,298 | 7/1992 | Shum | 502/61 |
| 5,215,950 | 6/1993 | Bournonville et al. | 502/66 |
| 5,227,557 | 7/1993 | Bournonville et al. | 585/419 |
| 5,268,522 | 12/1993 | Bournonville et al. | 585/415 |
| 5,281,566 | 1/1994 | Marcilly et al. | 502/61 |

FOREIGN PATENT DOCUMENTS

| | | |
|---|---|---|
| 754019 | 1/1971 | Belgium . |
| 361424 | 4/1990 | European Pat. Off. . |
| 47-42254 | 10/1972 | Japan . |
| 3-262539 | 11/1991 | Japan . |
| 7001852 | 8/1969 | Netherlands . |

*Primary Examiner*—Anthony McFarlane
*Assistant Examiner*—Walter D. Griffin

[57] ABSTRACT

Disclosed are reactions for the aromatization of hydrocarbons containing 2 to 9 carbon atoms per molecule, with a composite catalyst containing:

an MFI zeolite in hydrogen form, the framework containing at least one of the elements silicon, aluminum and/or gallium; a matrix; gallium; at least one noble metal of the platinum family, at least one additional metal selected from the group made up of tin, germanium, indium, copper, iron, molybdenum, gallium, thallium, gold, silver, ruthenium, chromium, tungsten and lead, and possibly a compound selected from the group made up of alkali and alkaline earth metals.

10 Claims, No Drawings

CATALYST OF THE GALLOALUMINOSILICATE TYPE CONTAINING GALLIUM, A NOBEL METAL OF THE PLATINUM FAMILY AND AT LEAST ON ADDITIONAL METAL, AND ITS USE IN THE AROMATIZATION OF HYDROCARBONS

This application is a division of application Ser. No. 07/863,658, filed Apr. 6, 1992, now U.S. Pat. No. 5,281,566.

The invention concerns a catalyst, a so-called composite catalyst, containing:

an MFI zeolite in hydrogen form, the framework of which contains silicon and at least one element from the group formed by aluminium and gallium, a matrix, gallium, at least one noble metal from the platinum family, at least one additional metal from the group made up of tin, germanium, indium, lead, gallium and thallium, group VIII metals such as copper, gold, silver, nickel, ruthenium and iron, and group VI metals such as chromium, molybdenum and tungsten, and possibly at least one compound from the group made up of alkali and alkaline earth metals (these metals, except for gallium, will hereinafter be referred to as "metals"), and its preparation and use in reactions for aromatising hydrocarbons containing 2 to 9 carbon atoms per molecule.

Catalysts based on zeolites which are doped with gallium, zinc or platinum are known to be active and selective in aromatising propane and butane. Hydrocarbons with more than 6 carbon atoms per molecule are conventionally converted to aromatics by catalytic reforming, using catalysts of the acid alumina type doped with platinum, and tin or rhenium may, for example, be added to that metal. These reforming catalysts nevertheless have a poor performance in the aromatisation of hydrocarbons containing less than 6 carbon atoms per molecule. The search for catalysts which will be effective in aromatising cuts rich in hydrocarbons of the $C_2$–$C_9$ type is therefore of great practical importance.

The reaction for the aromatisation of hydrocarbons containing less than 9 carbon atoms per molecule in the presence of zeolites has already been described in patents and publications. Several catalytic systems based on MFI zeolite are claimed; they may be distinguished by the additions which they contain. Essentially they can be divided into:

(i) systems containing gallium, and (ii) systems containing zinc.

These systems all have a serious defect, namely high selectivity for methane. Several solutions have been put forward to improve the performance of these catalytic systems, including the addition of platinum (Z. Jin, Y. Makino, A. Miyamoto. T. Inui, Chem. Express 2, p.515, 1987). The use of a non-acid MFI zeolite doped with various metallic elements has also been claimed (Y. Chen et al., WO 8904818).

Applicants have recently discovered (French patent application 90/10451) that if composite catalysts are used, containing firstly an MFI zeolite and secondly a generally amorphous carrier or matrix, with a noble metal of the platinum family and at least one additional metal, such as tin, lead or indium deposited on it, the carrier possibly also containing at least one alkali metal or alkaline earth metal (such as lithium or potassium), the catalytic performance obtained in reactions for aromatising paraffins with 2 to 9 carbon atoms will be far superior to that obtained with prior art systems.

If such catalysts are used it is possible, in particular, to limit reactions leading to the formation of methane, a product which is not required.

The research work carried out by Applicants has led to the surprising discovery that, if a composite catalyst is used, containing an MFI zeolite in hydrogen form, gallium in oxide form, a generally amorphous matrix and, deposited on that matrix, at least one noble metal of the platinum family (palladium, platinum, nickel), at least one additional metal from the group made of up of tin, germanium, lead, indium, lead, gallium and thallium, group VIII metals such as copper, gold, silver, nickel, ruthenium, iron and group VI metals such as chromium, molybdenum and tungsten, the matrix possibly also containing at least one alkali or alkaline earth metal (preferably lithium or potassium) the catalytic performance obtained in reactions for aromatising paraffins containing 2 to 9 carbon atoms per molecule will be far superior to that obtained with prior art catalysts.

The MFI zeolite contained in the catalyst of the present invention may be prepared by any methods described in prior art. Thus the zeolite may be synthesised in a conventional OH$^-$ medium in the presence or absence of an organic agent and/or alcohol. The document "Synthesis of high silica zeolites, P. Jacobs and J. Martens, Studies in Surface Science and Catalysis, Vol. 33, 1987" describes conventional synthesis of MFI zeolite. The MFI zeolite used in the invention may equally have been synthesised in less conventional media, such as a fluoride medium, in the presence of an organic compound (Patent EP-A-172068) or in the absence thereof (French patent application 90/16529). The crystallised framework of the zeolite used in the invention contains silicon and at least one element from the group formed by aluminium and gallium.

After the synthesising stage the MFI zeolite is converted to a hydrogen form, written as H-MFI, by removing virtually all the organic compounds and/or the alkali metal or alkaline earth metal cations which the synthesised zeolite may contain. Any of the methods described in prior art for putting it into the hydrogen form may be used, for example ion exchange, and these may or may not be followed by calcination or various chemical treatments.

Any zeolites synthesised in one of the following systems: Si—Al, Si—Al—Ga, Si—Ga are suitable for the invention. However, their Si/T ratio—where T represents Al and/or Ga—is generally over 7:1, preferably over 25:1 and still more preferably from 40–500:1.

The H-MFI zeolite used in the invention may be treated in that form by deposition of gallium; alternatively it may be mixed with the other constituents of the catalyst, and the gallium can be added to the mixture subsequently.

Many methods of depositing gallium may be used in the invention, including:

ion exchange using gallium salts in aqueous solution, for example gallium nitrate, gallium chloride or gallium hydroxide, impregnations with solutions of said gallium salts.

The content of gallium deposited on the composite catalyst is from 0.01 to 10% by weight and preferably from 0.03 to 4% by weight.

The matrix includes at least one refractory oxide and particularly at least one oxide of a metal from the group made up of magnesium, aluminium, titanium, zirconium, thorium, silicon and boron. It may additionally include charcoal.

The preferred matrix is alumina, with a specific surface area advantageously from 10–600 m$^2$/g and preferably from 150 to 400 m$^2$/g.

The composited catalyst of the invention may be prepared by two methods which are described theoretically below; the practical procedure for carrying them out is known to persons skilled in the art.

First Method

The H-MFI zeolite is mixed with the matrix. The mixture may be made from two powders, two previously structured solids or from a powder and a previously structured solid. The two solids may equally be structured together by any of the processes described in prior art: pelleting, extrusion, tableting, coagulation in drops or spray-drying. During these structuring operations a structuring additive, selected from the group made up of silica and alumina, may be added if necessary. Thus the zeolite has been mixed with the matrix and structuring has been carried out. After mixing and structuring the procedure is to deposit the metals and gallium on the body made up of the matrix and zeolite; the order in which they are deposited is not important. The majority of the metals, i.e. 30–100% by weight and preferably 60–100% by weight relative to the composite catalyst, is then considered to be on the matrix.

Second method

The metals are first deposited on the matrix, and the gallium on the H-MFI zeolite. The H-MFI zeolite containing the gallium is then mixed with the matrix containing the metals and they are structured; structuring is carried out under the same conditions as previously. In an alternative method the zeolite with the gallium deposited on it may be mixed with the matrix at any stage in the deposition of the metals thereon.

The preferred method of preparation comprises depositing the gallium on the zeolite, depositing the metals on the matrix, then including the zeolite filled with gallium in the matrix filled with metals by structuring the two powders. Structuring is preferably carried out after micronisation, which may be carried out by applying the wet grinding process.

The composite catalyst contains from 1 to 99% by weight of zeolite, the balance to 100% being made up of the matrix, the metals and the gallium. The respective proportions of zeolite and matrix vary widely, since they depend both on the Si/T ratio of the zeolite, where T is Al and/or Ga, and also on the metal content of the matrix in the case of the preferred method of preparation.

In the case of the preferred method of preparation, the matrix containing the metals is generally prepared by the procedures described in French patent application 90/10451, part of which is reproduced below.

The metals are impregnated either with a solution of all the metals which are to be included or with separate solutions of the noble metal of the platinum family, of the additional metal, and possibly of the element selected from the group made up of alkali and alkaline earth metals. When a plurality of solutions are used, intermediate drying and/or calcination may be carried out. The procedure normally ends with calcination, for example from 500°–1000° C., preferably in the presence of molecular oxygen, for example by scavenging with air.

The noble metal of the platinum family may be incorporated in the matrix by impregnating the matrix with an aqueous or non-aqueous solution containing a salt or compound of the noble metal. Platinum is generally included in the matrix in the form of chloroplatinic acid, although ammonia compounds or compounds such as ammonium chloroplatinate, di-carbonyl platinumdichloride, hexahydroxyplatinic acid, palladium chloride or palladium nitrate may equally be used for any noble metal.

The additional metal from the group made up of tin, germanium, lead, indium, lead, gallium and thallium, group VIII metals such as copper, gold, silver, nickel, ruthenium, iron, and group VI metals such as chromium, molybdenum and tungsten may be included in the form of compounds such as tin chlorides, bromides and nitrates, lead halides, nitrate, acetate and carbonate, germanium chloride and oxalate or indium nitrate and chloride.

The element from the group made up of alkali and alkaline earth metals, preferably lithium or potassium, may be included in the form of compounds such as the halide, nitrate, carbonate, cyanide or oxalate of said element.

A method of preparation, described in detail below, may for example comprise the following stages:

a) Putting at least one element from the group made up of alkali and alkaline earth metals on the matrix.

b) Calcining the product obtained at stage a).

c) Putting at least one noble metal of the platinum family on the matrix.

d) Calcining the product obtained at stage c).

e) Putting at least one additional metal M on the product obtained at s rage d).

If an alkali or alkaline earth metal is not used, only stages c), d) and e) of the process are carried out.

The use of at least one noble metal of the platinum family in the invention may take place, for example, in the form of ammonia compounds.

In the case of platinum, some examples of compounds which may be used are salts of platinum IV hexamines of the formula $Pt(NH_3)_6X_4$; salts of platinum IV halopentamines of the formula $(PtX(NH_3)_5)X_3$; salts of platinum N tetrahalodiamines of the formula $PtX_4(NH_3)_2$; platinum complexes with halo-polyketones and halogen compounds of the formula $H(Pt(aca)_2X)$; X being a halogen from the group formed by chlorine, fluorine, bromine and iodine and preferably being chlorine, and aca representing the formula $C_5H_7O_2$ residue derived from acetylacetone.

The noble metal of the platinum family is preferably incorporated through impregnation with an aqueous or organic solution of one of the above-mentioned organometallic compounds. Organic solvents which may be used include paraffinic, naphthene or aromatic hydrocarbons and organic halogen compounds, for example with from to 12 carbon atoms per molecule. Some examples are n-heptane, methylcyclohexane, toluene and chloroform. Mixtures of solvents may also be used.

When the noble metal of the platinum family has been incorporated, the product obtained is possibly dried and is then calcined, preferably at a temperature of 400°–1000° C.

After this calcination at least one additional metal is introduced. Its introduction is possibly preceded by reduction with hydrogen at a high temperature, e.g. from 300°–500° C. The additional metal M may be introduced in the form of at least one organic compound from the group made up of complexes of said metal, particularly polyketone complexes of the metal M and hydro carbyl metals such as metal alkyls, cycloalkyls, aryls, alkylaryls and arylalkyls.

The metal M is advantageously incorporated using a solution of the organometallic compound of said metal in an organic solvent. Organohalogen compounds of the metal M may equally be used. Some special examples of compounds of the metal M are tetrybutyl tin in cases where M is tin, tetraethyl lead in cases where M is lead and triphenyl indium in cases where M is indium.

The impregnating solvent is selected from the group made up of paraffinic, naphthene or aromatic hydrocarbons containing 6 to 12 carbon atoms per molecule and organic halogen compounds containing 1 to 12 carbon atoms per molecule. Some examples are n-heptane, methylcyclohexane and chloroform. Mixtures of the solvents defined above may also be used.

In cases where the preparation method described above is not used, it is possible to introduce at least one additional metal M before at least one noble metal of the platinum family. If the metal M is introduced before the noble metal, the compound of the metal M used is generally selected from the group made up of the halide, nitrate, acetate, tartrate, carbonate and oxalate of the metal M. It is then advantageously introduced in aqueous solution. In this case calcination in air at a temperature from 400° to 1000° C. is carried out before the introduction of at least one noble metal.

The composite catalyst contains:
1) by weight relative to the matrix:
   from 0.01 to 2%, preferably from 0.1 to 0.5%, of at least one noble metal of the platinum family.
   from 0.005 to 2%, preferably from 0.01 to 0.5% of tin in cases where the catalyst contains tin, and from 0.005 to 0.7%, preferably
   from 0.01 to 0.6% of at least one metal selected from the group made up of germanium, indium, lead, gallium and thallium, group VIII metals such as copper, gold, silver, nickel, ruthenium, iron and group VI metals such as chromium, molybdenum and tungsten, in cases where the catalyst contains at least one additional metal from said group, the total content of selected metals in the entity formed by tin and said group being from 0.02 to 1.20%, preferably from 0.02 to 1% and still more preferably from 0.03 to 0.80%.
   possibly from 0.01 to 4% and preferably from 0.1 to 0.6% of at least one metal from the group made up of alkali and alkaline earth metals, preferably selected from the group made up of lithium and potassium.
2) from 1 to 99% by weight of hydrogen-form MFI zeolite and
3) from 0.01 to 10%, preferably from 0.03 to 4% by weight of gallium.

In the method of the invention, when preparation is completed the structured catalyst contains an H-MFI zeolite, gallium, metals and a matrix. The procedure is then to calcine it in air at a temperature from 450° to 1000° C. The catalyst thus calcined may advantageously undergo activating treatment in hydrogen at high temperature, e.g. from 300° to 500° C. The procedure for treatment in hydrogen may, for example, comprise gradually raising the temperature in a stream of hydrogen up to the maximum reducing temperature, generally from 300° to 500° C. and preferably from 350° to 450° C., then keeping the catalyst at that temperature for a period generally of 1 to 6 hours.

The catalyst of the invention as described above is used to aromarise alkanes containing 2 to 9 carbon atoms per molecule, whether or not olefins are present. This reaction is particularly important since it may, for example, enable residues from refining operations to be upgraded by converting them to products with a higher added value (benzene, toluene and xylenes) while also contributing to the production of large quantities of hydrogen, which are indispensable, e.g. for hydro treatment processes.

The charge which includes compounds containing 2 to 9 carbon atoms per molecule is put into contact with the catalyst of the invention at a temperature of from 400° to 700° C.

The following examples clarify the invention but without restricting its scope.

Example 1 preparation of alumina containing platinum, tin and lithium (catalyst A).

The alumina used has a specific surface area of 240 m$^2$/g and a pore volume of 0.48 cm$^3$/g.

100 cm$^3$ of an aqueous solution of lithium nitrate is added to 100 g of alumina carrier.

They are left in contact for 6 hours, drained, dried for 1 hour at 100°–120° C., then calcined for 2 hours at 530° C.

The calcined product containing lithium is then impregnated with tin: an aqueous solution of tin acetate is put into contact with the alumina carrier, in quantities of 100 cm$^3$ of solution per 100 g of carrier, for 6 hours. The solid obtained is then drained, dried for 1 hour at 100°–120° C. then calcined at 530° C.

The calcined solid containing lithium and tin is then impregnated with platinum, by adding 100 cm$^3$ of a solution of platinum acetylacetonate in toluene to the solid. The platinum concentration of the solution is equal to 3 g/l. They are left in contact for 6 hours, dried for 1 hour at 100°–120° C. then calcined for 2 hours at 530° C. Reduction is thereupon carried out in a stream of dry nitrogen for 2 hours at 450° C.

The alumina then contains 0.30% of platinum, 0.3% of tin and 0.5% of lithium by weight.

Example 2 preparation of alumina containing platinum, tin and lithium (catalyst B).

100 cm$^3$ of an aqueous solution of lithium nitrate is added to 100 g of alumina carrier. They are left in contact for 6 hours, drained, dried in 1 hour at 100°–120° C. then calcined in a stream of dry air for 2 hours at 530° C.

The calcined product containing lithium is impregnated with platinum in the same way as product A.

After reduction the product containing lithium and platinum is submerged in n-heptane in quantities of 100 g of solid per 300 cm$^3$ of hydrocarbon solvent. 3 g of a solution of tetra-n-butyl tin in n-heptane (solution containing 10% by weight of tin) is injected in the n=heptane containing the catalyst. The solid containing the platinum and the tetra-n-butyl tin solution are kept in contact for 6 hours at the reflux temperature of the heptane. The impregnating solution is then removed and the solid is washed three times with pure n-heptane at the reflux temperature of the n-heptane. The catalyst is dried. It then undergoes calcination in air for 2 hours at 500° C. followed by reduction in a stream of hydrogen at 450° C. before being put in the reactor.

The alumina then contains 0.3% of platinum, 0.3% of tin and 0.5% of lithium by weight.

Example 3 hydrogen-form MFI zeolite, and catalyst C containing that H-MFI zeolite and gallium.

A hydrogen-form H-MFI zeolite is used, supplied by CONTEKA under reference CBV 1502. It is characterised by an Si/Al ratio of 75, a sodium content of 0.016% by weight and a pore volume, measured by nitrogen adsorption at 77K, of 0.174 cm$^3$/g.

The gallium is deposited on the zeolite by ion exchange. The exchange solution is prepared from gallium nitrate $Ga(NO_3)_3$ with a normality of 0.15N.

The pH of the gallium nitrate solution is adjusted to a value of 2 by adding ammonia.

The gallium content reached in catalyst C thus obtained, after three successive ion exchanges of H-MFK zeolite with the solution described above, is 3.3% by weight.

Example 4

A charge comprising a mixture of hydrocarbons containing 5 to 6 carbon atoms per molecule is to be converted. For this purpose one of the following catalysts must be present: a catalyst formed by the H=MFI zeolite described in example 3, either alone or mixed with catalyst A from example 1 or mixed with catalyst B from example 2; and catalyst C from example 3, either alone or mixed with catalyst A from example 1 or mixed with catalyst B from example 2. The mixtures are all equal-mass mixtures, and they are used after being pelleted.

These catalysts are tested in the conversion of a $C_5$–$C_6$ charge of the following composition (expressed in % by weight):

| Paraffins | $C_5$ | 90% |
|---|---|---|
|  | $C_6$ | 5.4% |
| Naphthenes | $C_5$ | 3.7% |
|  | $C_6$ | 0.9% |

The operating conditions are as follows:

| temperature | 480° C. |
|---|---|
| pressure | 2.5 bars |
| pph | 3 h$^{-1}$ |

The results of the test are set out in table 1.

TABLE 1

| Catalyst | conversion (% by weight) | Selectivity (% by weight) | | | | |
|---|---|---|---|---|---|---|
| | | $CH_4$ | $C_2H_6+$ $C_2H_4$ | $C_3H_8+$ $C_3H_6$ | $C_4H_{10}$ | Aromatics |
| MFI zeolite (comparative) | 92 | 30 | 25 | 15 | 20 | 10 |
| Catalyst C (comparative) | 93 | 7 | 18 | 29 | 8 | 38 |
| Mixture: 50% cata. A 50% H-MFI zeolite | 90 | 6 | 12 | 14 | 8 | 60 |
| Mixture: 50% cata. B 50% H-MFI zeolite | 92 | 5 | 11 | 15 | 7 | 62 |
| Mixture: 50% cata. A 50% cata. C | 91 | 6 | 9 | 15 | 7 | 63 |
| Mixture: 50% cata. B 50% cata. C | 93 | 5 | 9 | 14 | 8 | 64 |

TABLE 1-continued

| Catalyst | conversion (% by weight) | Selectivity (% by weight) | | | | |
|---|---|---|---|---|---|---|
| | | $CH_4$ | $C_2H_6+$ $C_2H_4$ | $C_3H_8+$ $C_3H_6$ | $C_4H_{10}$ | Aromatics |

Thus it will be seen that the catalyst A-catalyst C and catalyst B-catalyst C mixtures according to the invention give improved selectivity for aromatics.

We claim:

1. A process for aromatization of hydrocarbons, comprising subjecting a hydrocarbon feed to aromatization conditions in the presence of a catalyst, wherein the catalyst comprises:

from 1–99% by weight of an MFI zeolite in hydrogen form, the framework of which contains silicon and at least one of aluminum or gallium, a matrix, a catalytically effective amount of gallium, a catalytically effective amount of at least one noble metal of the platinum family, and a catalytically effective amount of at least one additional metal which is tin, germanium, indium, lead, gallium, thallium, a Group VIII metal, copper, gold, silver, or a Group VI metal.

2. The process of claim 1, wherein said catalyst contains, by weight relative to the matrix:

from 0.01 to 2% of at least one noble metal of the platinum family, from 0.005 to 2% of tin in cases where the catalyst contains tin, or from 0.005 to 0.7% of germanium, indium, lead, gallium, thallium, group VIII metals, copper, gold, silver, ruthenium or group VI metals, the total content of metals being from 0.02 to 1.20%.

3. A process of claim 1, wherein the catalyst contains at least one alkali metal or alkaline earth metal.

4. The process of claim 1, wherein the catalytically effective amount of gallium in the catalyst is from 0.01 to 10% by weight.

5. The process of claim 2, wherein the catalyst contains, by weight relative to the matrix:

from 0.01 to 4% of alkali metals or alkaline earth metals.

6. The process of claim 1, wherein in the catalyst the matrix is alumina.

7. The process of claim 2, wherein the group VIII metals are nickel or iron and the group VI metals are chromium, molybdenum or tungsten.

8. A process for aromatization of hydrocarbons, comprising subjecting a hydrocarbon feed to aromatization conditions in the presence of a catalyst, wherein the catalyst comprises:

from 1–99% by weight of an MFI zeolite in hydrogen form, the framework of which contains silicon and at least one of aluminum or gallium, a matrix, a catalytically effective amount of gallium, a catalytically effective amount of at least one noble metal of the platinum family, and a catalytically effective amount of at least one additional metal which is tin, germanium, indium, lead, gallium, thallium, a Group VIII metal, copper, gold, silver, or a Group VI metal, and wherein said catalyst is prepared by a process comprising mixing the zeolite with the matrix and structuring the zeolite and matrix, then depositing the metals and gallium and calcining to produce the catalyst.

9. The process of claim 8, wherein calcination of the catalyst is followed by activation in hydrogen.

10. A process for aromatization of hydrocarbons, comprising subjecting a hydrocarbon feed to aromatization conditions in the presence of a catalyst, wherein the catalyst comprises:

from 1–99% by weight of an MFI zeolite in hydrogen form, the framework of which contains silicon and at least one of aluminum or gallium, a matrix, a catalytically effective amount of gallium, a catalytically effective amount of at least one noble metal of the platinum family, and a catalytically effective amount of at least one additional metal which is tin, germanium, indium, lead, gallium, thallium, a Group VIII metal, copper, gold, silver, or a Group VI metal, and wherein said catalyst is prepared by a process comprising previously depositing the catalyst metals on the matrix and the gallium on the zeolite, mixing the MFI zeolite with the matrix, and structuring and carrying out calcination.

* * * * *